(12) United States Patent
Van Eijk et al.

(10) Patent No.: US 8,685,650 B2
(45) Date of Patent: *Apr. 1, 2014

(54) METHOD FOR THE IDENTIFICATION OF THE CLONAL SOURCE OF A RESTRICTION FRAGMENT

(71) Applicant: Keygene N.V., Wageningen (NL)

(72) Inventors: Michael Josephus Theresia Van Eijk, Herpen (NL); Taco Peter Jesse, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/783,601

(22) Filed: Mar. 4, 2013

(65) Prior Publication Data

US 2013/0184166 A1 Jul. 18, 2013

Related U.S. Application Data

(60) Continuation of application No. 13/344,162, filed on Jan. 5, 2012, now Pat. No. 8,394,591, which is a division of application No. 12/373,220, filed as application No. PCT/NL2007/000177 on Jul. 10, 2007, now Pat. No. 8,178,300.

(60) Provisional application No. 60/830,121, filed on Jul. 12, 2006.

(51) Int. Cl.
*C12Q 1/68* (2006.01)
*C12P 19/34* (2006.01)

(52) U.S. Cl.
USPC .......................................... 435/6.12; 435/91.2

(58) Field of Classification Search
USPC ................................................ 435/6.12, 91.2
See application file for complete search history.

(56) References Cited

U.S. PATENT DOCUMENTS

| 6,480,791 B1 | 11/2002 | Strathmann |
| 7,935,488 B2 | 5/2011 | Zabeau et al. |

FOREIGN PATENT DOCUMENTS

| WO | WO 00/24937 A2 | 5/2000 |
| WO | WO 2004/063323 | 7/2004 |
| WO | WO 2006/137734 | 12/2006 |

OTHER PUBLICATIONS

Accelerated Examination Support Document, filed in the USPTO on Oct. 5, 2010 in U.S. Appl. No. 12/484,541.
Baird, et al., "Rapid SNP Discovery and Genetic Mapping Using Sequenced RAD Markers", *PLoS ONE*, Oct. 2008, vol. 3, issue 10, e3376, pp. 1-7.
Bouzidi, et al., "A sunflower BAC library suitable for PCR screening and physical mapping of targeted genomic regions.", TAG, vol. 113, No. 1, 2006, pp. 81-89.

(Continued)

*Primary Examiner* — Kenneth Horlick
(74) *Attorney, Agent, or Firm* — Foley & Lardner LLP; Richard C. Peet

(57) ABSTRACT

The present invention relates to a high throughput method for the identification and detection of molecular markers wherein restriction fragments are generated and suitable adaptors comprising (sample-specific) identifiers are ligated. The adapter-ligated restriction fragments may be selectively amplified with adaptor compatible primers carrying selective nucleotides at their 3' end. The amplified adapter-ligated restriction fragments are, at least partly, sequenced using high throughput sequencing methods and the sequence parts of the restriction fragments together with the sample-specific identifiers serve as molecular markers.

17 Claims, 5 Drawing Sheets

(56) References Cited

OTHER PUBLICATIONS

International Search Report for International Application No. PCT/NL2007/000177, dated Nov. 29, 2007. (3 pgs.)

European Search Report for European Patent Application No. 10176619, dated Oct. 29, 2010 (3 pages).

Jamsari, et al., "BAC-derived diagnostic markers for sex determination in asparagus.", Theoretical and Applied Genetics, vol. 108, No. 6, 2004, pp. 1140-1146.

Klein et al., "A High-throughput AFLP-based Method for Constructing Integrated Genetic and Physical Maps: Progress Toward a Sorghum Genome Map", *Genome Research*, Jun. 2000, pp. 789-807, I. 10, No. 6, Cold Spring Harbor Laboratory Press.

Klein, et al., "A high-throughput AFLP-based method for constructing integrated genetic and physical maps: Progress toward a sorghum genome map", Genome Research, vol. 10, No. 5, 2000, pp. 789-807.

Lewis, et al., "High-Density Detection of Restriction-Site-Associated DNA Markers for Rapid Mapping of Mutated Loci in Neurospora", *Genetics*, Oct. 2007, vol. 177, pp. 1163-1171.

Miller, et al., "RAD marker microarrays enable rapid mapping of zebrafish mutations", *Genome Biology*, 2007, vol. 8, Issue 6, Article R105.

Miller, et al., "Rapid and cost-effective polymorphism identification and genotyping using restriction site associated DNA (RAD) markers", *Genome Research*, 2007, vol. 17, pp. 240-248.

PCT International Preliminary Report on Patentability, dated Jan. 13, 2009, 6 pages.

Vos, et al., "AFLP: a new technique for DNA fingerprinting", Nucleic Acids Research, 1995, vol. 23, No. 2, pp. 4407-4414.

Xia, et al., "Construction and characterization of a BAC library of soybean.", vol. 141, No. 1-2, 2005, pp. 129-137.

FIG 4 Unique adress for each pool coordinate

METHOD FOR THE IDENTIFICATION OF THE CLONAL SOURCE OF A RESTRICTION FRAGMENT

CROSS-REFERENCE TO RELATED APPLICATIONS

This application is a Divisional of U.S. patent application Ser. No. 13/344,162, now U.S. Pat. No. 8,394,591 issued on Mar. 12, 2013 which is a divisional of U.S. patent application Ser. No. 12/373,220 filed Mar. 11, 2011, Issued as U.S. Pat. No. 8,178,300 on May 15, 2012, which is a U.S. National Stage of PCT/NL2007/000177, filed Jul. 10, 2001, which claims the benefit of U.S. Provisional Application No. 60/830,121, filed Jul. 12, 2006, all of which are incorporated herein by reference in entirety.

FIELD OF THE INVENTION

The present invention relates to the field of molecular biology and biotechnology. In particular, the invention relates to the field of nucleic acid detection and identification. More in particular the invention relates to the generation of a physical map of a genome, or part thereof, using high-throughput sequencing technology.

BACKGROUND OF THE INVENTION

Integrated genetic and physical genome maps are extremely valuable for map-based gene isolation, comparative genome analysis and as sources of sequence-ready clones for genome sequencing projects. The effect of the availability of an integrated map of physical and genetic markers of a species for genome research is enormous. Integrated maps allow for precise and rapid gene mapping and precise mapping of microsatellite loci and SNP markers. Various methods have been developed for assembling physical maps of genomes of varying complexity. One of the better characterized approaches use restriction enzymes to generate large numbers of DNA fragments from genomic subclones (Brenner et al., Proc. Natl. Acad. Sci., (1989), 86, 8902-8906; Gregory et al., Genome Res. (1997), 7, 1162-1168; Marra et al., Genome Res. (1997), 7, 1072-1084). These fingerprints are compared to identify related clones and to assemble overlapping clones in contigs. The utility of fingerprinting for ordering large insert clones of a complex genome is limited, however, due to variation in DNA migration from gel to gel, the presence of repetitive DNAs, unusual distribution of restriction sites and skewed clone representation. Most high quality physical maps of complex genomes have therefore been constructed using a combination of fingerprinting and PCR-based or hybridisation based methods. However, one of the disadvantages of the use of fingerprinting technology is that it is based on fragment-pattern matching, which is an indirect method.

It would be preferred to create physical maps by generating the contigs based on actual sequence data, i.e. a more direct method. A sequence-based physical map is not only more accurate, but at the same time also contributes to the determination of the whole genome sequence of the species of interest. Recently methods for high throughput sequencing have been made available that would allow for the determination of complete nucleotide sequences of clones in a more efficient and cost-effective manner.

However, detection by sequencing of the entire restriction fragment is still relatively uneconomical. Furthermore, the current state of the art sequencing technology such as disclosed herein elsewhere (from 454 Life Sciences, www.454.com, Solexa, www.solexa.com, and Helicos, www.helicosbio.com), despite their overwhelming sequencing power, can only provide sequencing fragments of limited length. Also the current methods do not allow for the simultaneous processing of many samples in one run.

It is now the goal of the present invention to devise and describe a strategy that allows for the high throughput generation of a physical map based on a combination of restriction digestion, pooling, highly accurate amplification and high throughput sequencing. Using this method, physical maps can be generated, even of complex genomes.

DEFINITIONS

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Nucleic acid: a nucleic acid according to the present invention may include any polymer or oligomer of pyrimidine and purine bases, preferably cytosine, thymine, and uracil, and adenine and guanine, respectively (See Albert L. Lehninger, Principles of Biochemistry, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

AFLP: AFLP refers to a method for selective amplification of nucleic acids based on digesting a nucleic acid with one or more restriction endonucleases to yield restriction fragments, ligating adaptors to the restriction fragments and amplifying the adaptor-ligated restriction fragments with at least one primer that is (in part) complementary to the adaptor, (in part) complementary to the remains of the restriction endonuclease, and that further contains at least one randomly selected nucleotide from amongst A, C, T, or G (or U as the case may be). AFLP does not require any prior sequence information and can be performed on any starting DNA. In general, AFLP comprises the steps of:

(a) digesting a nucleic acid, in particular a DNA or cDNA, with one or more specific restriction endonucleases, to fragment the DNA into a corresponding series of restriction fragments;
 (b) ligating the restriction fragments thus obtained with a double-stranded synthetic oligonucleotide adaptor, one end of which is compatible with one or both of the ends of the restriction fragments, to thereby produce adaptor-ligated, preferably tagged, restriction fragments of the starting DNA;
 (c) contacting the adaptor-ligated, preferably tagged, restriction fragments under hybridizing conditions with one or more oligonucleotide primers that contain selective nucleotides at their 3'-end;
(d) amplifying the adaptor-ligated, preferably tagged, restriction fragment hybridised with the primers by PCR or a similar technique so as to cause further elongation of the hybridised primers along the restriction fragments of the starting DNA to which the primers hybridised; and
(e) detecting, identifying or recovering the amplified or elongated DNA fragment thus obtained.

AFLP thus provides a reproducible subset of adaptor-ligated fragments. AFLP is described in inter alia EP 534858, U.S. Pat. No. 6,045,994 and in Vos et al. (Nucleic Acid Research, 1995, 23, 21, 4407-4414) Reference is made to these publications for further details regarding AFLP. The AFLP is commonly used as a complexity reduction technique and a DNA fingerprinting technology. Within the context of the use of AFLP as a fingerprinting technology, the concept of an AFLP marker has been developed.

Selective base: located at the 3' end of the primer that contains a part that is complementary to the adaptor and a part that is complementary to the remains of the restriction site, the selective base is randomly selected from amongst A, C, T or G. By extending a primer with a selective base, the subsequent amplification will yield only a reproducible subset of the adaptor-ligated restriction fragments, i.e. only the fragments that can be amplified using the primer carrying the selective base. Selective nucleotides can be added to the 3' end of the primer in a number varying between 1 and 10. Typically 1-4 suffice and are preferred. Both primers may contain a varying number of selective bases. With each added selective base, the number of amplified adaptor-ligated restriction fragments (amplicons) in the subset is reduced by a factor of about 4. Typically, the number of selective bases used in AFLP is indicated by +N+M, wherein one primer carries N selective nucleotides and the other primers carries M selective nucleotides. Thus, an Eco/Mse+1/+2 AFLP is shorthand for the digestion of the starting DNA with EcoRI and MseI, ligation of appropriate adaptors and amplification with one primer directed to the EcoRI restricted position carrying one selective base and the other primer directed to the MseI restricted site carrying 2 selective nucleotides. A primer used in AFLP that carries at least one selective nucleotide at its 3' end is also depicted as an AFLP-primer. Primers that do not carry a selective nucleotide at their 3' end and which in fact are complementary to the adaptor and the remains of the restriction site are sometimes indicated as AFLP+0 primers.

Clustering: with the term "clustering" is meant the comparison of two or more nucleotide sequences based on the presence of short or long stretches of identical or similar nucleotides and grouping together the sequences with a certain minimal level of sequence homology based on the presence of short (or longer) stretches of identical or similar sequences.

Assembly: construction of a contig based on ordering a collection of (partly) overlapping sequences, also called "contig building".

Alignment: positioning of multiple sequences in a tabular presentation to maximize the possibility for obtaining regions of sequence identity across the various sequences in the alignment, e.g. by introducing gaps. Several methods for alignment of nucleotide sequences are known in the art, as will be further explained below.

Identifier: a short sequence that can be added an adaptor or a primer or included in its sequence or otherwise used as label to provide a unique identifier. Such a sequence identifier (tag) can be a unique base sequence of varying but defined length uniquely used for identifying a specific nucleic acid sample. For instance 4 bp tags allow 4(exp4)=256 different tags. Typical examples are ZIP sequences, known in the art as commonly used tags for unique detection by hybridization (Iannone et al. Cytometry 39:131-140, 2000). Using such an identifier, the origin of a PCR sample can be determined upon further processing. In the case of combining processed products originating from different nucleic acid samples, the different nucleic acid samples are generally identified using different identifiers.

Sequencing: The term sequencing refers to determining the order of nucleotides (base sequences) in a nucleic acid sample, e.g. DNA or RNA.

High-throughput screening: High-throughput screening, often abbreviated as HTS, is a method for scientific experimentation especially relevant to the fields of biology and chemistry. Through a combination of modern robotics and other specialised laboratory hardware, it allows a researcher to effectively screen large amounts of samples simultaneously.

Restriction endonuclease: a restriction endonuclease or restriction enzyme is an enzyme that recognizes a specific nucleotide sequence (target site) in a double-stranded DNA molecule, and will cleave both strands of the DNA molecule at or near every target site.

Restriction fragments: the DNA molecules produced by digestion with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adaptors: short double-stranded DNA molecules with a limited number of base pairs, e.g. about 10 to about 50 base pairs in length, which are designed such that they can be ligated to the ends of restriction fragments. Adaptors are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adaptor molecule is designed such that it is compatible with the end of a restriction fragment and can be ligated thereto; the other end of the adaptor can be designed so that it cannot be ligated, but this need not be the case (double ligated adaptors).

Adaptor-ligated restriction fragments: restriction fragments that have been capped by adaptors.

Primers: in general, the term primers refer to DNA strands which can prime the synthesis of DNA. DNA polymerase cannot synthesize DNA de novo without primers: it can only extend an existing DNA strand in a reaction in which the complementary strand is used as a template to direct the order of nucleotides to be assembled. We will refer to the synthetic oligonucleotide molecules which are used in a polymerase chain reaction (PCR) as primers.

DNA amplification: the term DNA amplification will be typically used to denote the in vitro synthesis of double-stranded DNA molecules using PCR. It is noted that other amplification methods exist and they may be used in the present invention without departing from the gist.

SUMMARY OF THE INVENTION

The present inventors have found by using a combination of restriction enzyme digestion of clones in a library, adapter-ligation, (selective) amplification, high-throughput sequencing and deconvolution of the resulting sequences results in contigs that can be used to assemble physical maps, even of large and complex genomes.

DETAILED DESCRIPTION OF THE INVENTION

In one aspect, the invention relates to a method for the generation of a physical map of at least part of a genome comprising the steps of:
  (a) providing a sample DNA;
  (b) generating an artificial chromosome (BAC, YAC) clone bank wherein each artificial chromosome clone contains part of the sample DNA;
  (c) combining the artificial chromosome clones in one or more pools, wherein each clone is present in more than one pool, to create a library;
  (d) digesting the DNA of one or more pools with one or more restriction endonucleases to provide for a set of restriction fragments for each pool;
  (e) ligating adaptors to one or both sides of the restriction fragments, wherein at least one adaptor contains a pool-specific identifier or a degenerate identifier section, respectively, to provide adaptor-ligated restriction fragments;
  (f) optionally, combining the adapto-ligated restriction fragments;
  (g) amplifying the adaptor-ligated restriction fragments of step (e) with at least one primer, which primer contains a pool-specific section corresponding to the pool-specific identifier section in the adaptor or contains a pool-specific identifier at the position of the degenerate identifier section, respectively, to provide tagged amplified adaptor-ligated restriction fragments (amplicons);
  (h) optionally, combining the amplicons in a set of combined amplicons;
  (i) determining the sequence of at least the pool-specific identifier and part of the restriction fragment of the amplicons or set of combined amplicons;
  (j) assigning the restriction fragment sequences determined in the amplicons of step (i) to the corresponding clones using the pool-specific identifiers;
  (k) ordering the restriction fragments derived from the same clone to build a contig;
  (l) ordering the contigs of the clones of step (k) to thereby build a clone-contig and generate a physical map.

In step (a) of the method a sample DNA is provided. This can be achieved by any means in the art such as disclosed for instance by Sambrook et al (Sambrook and Russell (2001) "Molecular Cloning: A Laboratory Manual ($3^{rd}$ edition), Cold Spring Harbor Laboratory, Cold Spring Harbor Laboratory Press). The sample DNA can be from any species, in particular from human, plant or animal origin. It is possible to use only a part of a genome, but that is not necessary as the present invention also provides for methods to accommodate genomes of any size, for instance through the creation of reproducible subsets via selective amplification based on AFLP, as described herein elsewhere. Thus typically, the present method uses the entire genome.

In step (b) an artificial clone bank is generated. The library can be a Bacterial Artificial Chromosome library (BAC) or based on yeast (YAC). Other libraries such as based on cosmids, PAC, TAC or MAC are also possible. Preferred is a BAC library. The library is preferably of a high quality and preferably is a high insert size genomic library. This means that the individual BAC contains a large insert of the genomic DNA under investigation (typically >125 kbp). The size of the preferred large insert is species-dependent. Throughout this application reference is made to BACs as examples of artificial chromosomes. However, it is noted that the present invention is not limited thereto and that other artificial chromosomes can be used without departing from the gist of the invention. Preferably the libraries contain at least five genome equivalents, more preferably at least 7, most preferably at least 8. Particularly preferred is at least 10. The higher the number of genome equivalents in the library, the more reliable the resulting contigs and physical map will be.

The individual clones in the library are pooled to form pools containing a multitude of artificial chromosomes or clones. The pooling may be the simple combination of a number of individual clones into one sample (for example, 100 clones into 10 pools, each containing 10 clones), but also more elaborate pooling strategies may be used. The distribution of the clones over the pools is preferably such that each clone is present in at least two or more of the pools. Preferably, the pools contain from 10 to 10000 clones per pool, preferably from 100 to 1000, more preferably from 250 to 750. It is observed that the number of clones per pool can vary widely, and this variation is related to, for instance, the size of the genome under investigation. Typically, the maximum size of a pool or a sub-pool is governed by the ability to uniquely identify a clone in a pool by a set of identifiers. As will be further elaborated on hereinbelow, a typical range for a genome equivalent in a pool is in the order of 0.2-0.3, and this may again vary per genome. The pools are generated based on pooling strategies well known in the art. The skilled man is capable selecting the optimal pooling strategy based on factors such as genome size etc. The resulting pooling strategy will depend on the circumstances, and examples thereof are plate pooling, N-dimensional pooling such as 2D-pooling, 3D-pooling, 6D-pooling or complex pooling. To facilitate handling of large numbers of pools, the pools may, on their turn, be combined in super-pools (i.e. super-pools are pools of pools of clones) or divided into sub-pools, as is exemplified in the appending FIG. 1 where a 3D pooling is illustrated. Other examples of pooling strategies and their deconvolution (i.e. the correct identification of the individual clone in a library by detection of the presence of an known associated indicator (i.e. label or identifier) of the clone in one or more pools or subpools) are for instance described in U.S. Pat. No. 6,975,943 or in Klein et al. in Genome Research, (2000), 10, 798-807. The pooling strategy is preferably such that every clone in the library is distributed such over the pools that a unique combination of pools is made for every clone. The result thereof is that a certain combination of (sub)pools uniquely identifies a clone.

The pools are digested with restriction endonucleases to yield restriction fragments. Each pool is preferably separately subjected to an endonuclease digest. Each pool is treated with the same (combination of) endonuclease(s). In principle any restriction endonuclease can be used. Restriction endonucleases may be frequent cutters (4 or 5 cutters, such as MseI or PstI) or rare cutters (6 and more cutters such as EcoRI, HindIII). Typically, restriction endonucleases are selected such that restriction fragments are obtained that are, on average, present in an amount or have a certain length distribution that is adequate for the subsequent steps. In certain embodiments, two or more restriction endonucleases can be used and in certain embodiments, combinations of rare and frequent cutters can be used. For large genomes the use of, for instance, three or more restriction endonucleases can be used advantageously.

To one or both ends of the restriction fragments, adaptors are ligated in step (e) to provide for adaptor-ligated restriction fragments. Typically, adaptors are synthetic oligonucleotides as defined herein elsewhere. The adaptors used in the present invention preferably contain an identifier section, in essence as defined herein elsewhere. In certain embodiments, the adaptor contains a pool-specific identifier, i.e. for each pool, an adapter containing a unique identifier is used that unequivocally indicates the pool. In certain embodiments, the adaptor contains a degenerate identifier section which is used in combination with a primer containing a pool-specific identifier.

In certain embodiments, the adapter-ligated restriction fragments can be combined in larger groups, in particular when the adaptors contain a pool-specific identifier. This combination in larger groups may aid in reducing the number of parallel amplifications of each set of adapter-ligated restriction fragments obtained from a pool.

The adaptor-ligated restriction fragments can be amplified using a set of primers of which at least one primer contains a pool-specific identifier at the position of the pool-specific or degenerate identifier in the adaptor. This embodiment also allows for the grouping of adaptor-ligated restriction fragments prior to the amplification as outlined above. In an alternative embodiment, each pool of adaptor-ligated restriction fragments, wherein the adaptor contained a degenerate identifier section, is amplified separately using a set of primers of which at least one primer contains a pool specific section, thereby uniquely identifying the pool.

Either way, the result is a set of amplified adapter-ligated restriction fragments, also depicted as amplicons, that are linked to the pool from which they originate by the presence in the amplicon of the pool-specific identifier. In certain embodiments, sub-sets of amplicons may be created by selective amplification using primers carrying selective nucleotides at their 3' end, essentially as described herein elsewhere.

The amplicons may be combined in certain embodiments, in a set of combined amplicons or a so-called sequence library.

In step (i) of the method, the amplicons are subjected to sequencing, preferably high throughput sequencing as described herein below. During sequencing, at least part of the nucleotide sequence of the amplicons is determined. Preferably at least the sequence of the pool-specific identifier and part of the restriction fragment of the amplicons is determined. Preferably, a sequence of at least 10 nucleotides of the restriction fragment is determined In certain embodiments, at least 11, 12, 13, 14 or 15 nucleotides of the restriction fragment are determined The number of nucleotides that are to be determined minimally will be, again, genome dependent. For instance, in plants more repetitive sequences are present, hence longer sequences (25-30 bp) are to be determined. For instance, calculations on the known genome of *Arabidopsis* have shown that, when including a 6 bp restriction site in the sequencing step, about 20 bp per restriction fragment needs to be determined. It is possible to determine the sequence of the entire restriction fragment, but this is not an absolute necessity for contig building of a BAC clone.

In the sequencing step, to provide for increased accuracy, the sequence library may be sequenced with a coverage of at least 5. This means that the sequence is determined of at least 5 amplicons obtained from the amplification of one specific adaptor-ligated restriction fragment. In other words: each restriction fragment is (statistically) sequenced at least five times. Increased coverage is preferred as its improves accuracy further, so preferably coverage is at least 7, more preferably a least 10. Increased coverage is used to compensate for a phenomenon that is known as 'sampling variation'.

In the following step, the (partly) sequenced amplicons are correlated to the corresponding clone, typically in silico by means of computerized methods. The amplicons are selected that contain identical sections of nucleotides in the restriction fragment-derived part. Subsequently the different pool-specific identifiers are identified that are present in those amplicons. The combination of the different pool-specific identifiers and hence the sequence of the restriction fragment can be uniquely assigned to a specific clone (a process described earlier as 'deconvolution'). For example, in the case of a 3D pooling strategy (X,Y,Z), each pool in the library is uniquely addressed by a combination of 3 pool-specific identifiers. Each clone occurs more than once in the library, so for each occurrence of a clone in the library, a combination of 3 pool-specific identifiers can be made in combination with the same restriction fragment-derived section. In other words: a restriction fragment-derived section originating from a clone will be tagged with 3 different identifiers. Unique restriction fragment-derived sections, when observed in combination with the 3 identifiers can be assigned to a single BAC clone. This can be repeated for each amplicon that contains other unique sections of nucleotides in the restriction fragment-derived part. This process of deconvolution can be made easier by keeping the genome equivalent per pool relatively low (<0.3, pref. 0.2), thereby reducing the chance that the same fragment is present twice in the same pool derived from different clones. An exemplary representation of the pooling concept is provided in FIG. 1. A sample DNA is converted into BAC library. The BAC library is pooled in a set of pools (M) (3 pools are shown, each containing about 0.3 GE). Each pool is divided into (X+Y+Z) subpools (typically a stack of microtiterplates).

The sequenced amplicons that are now linked to a particular clone in the library are used in building a contig based on sequence matching of the restriction fragment derived sections. The contigs of each clone are then aligned to generate a physical map.

The advantages of the present method reside inter alia in the improved accuracy for BAC contig building compared to conventional technology for BAC contig building. Furthermore, physical map building based on sequence information is more accurate, as it is a direct way of physical map construction and contributes to the determination of the genome sequence, and further contributes sequence information suitable for STS development and comparative mapping purposes.

The high throughput sequencing used in the present invention is a method for scientific experimentation especially relevant to the fields of biology and chemistry. Through a combination of modern robotics and other specialised laboratory hardware, it allows a researcher to effectively screen large amounts of samples simultaneously.

It is preferred that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) Proc. Natl. Acad. Sci. USA 101:5488-93, and technologies of Helicos, Solexa, US Genomics, etcetera, which are herein incorporated by reference.

454 Life Sciences Technology

In certain embodiments, it is preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described allows sequencing of 20 to 40 million bases in a single run and is 100 times faster and cheaper than competing technology. The sequencing technology essentially contains 5 steps: 1) fragmentation of DNA and ligation of specific adaptors to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of /enrichment for beads containing amplified ssDNA molecules on their surface 4) deposition of DNA carrying beads in a PicoTiter™ Plate; and 5) simultaneous sequencing in 100,000 wells by generation of a pyrophosphate light signal. The method will be explained in more detail below.

In a preferred embodiment, the sequencing comprises the steps of:
a. annealing adapted fragments to beads, each bead being annealed with a single adapted fragment;
b. emulsifying and amplifying the annealed fragments on the beads in water-in-oil microreactors, each water-in-oil microreactor comprising a single bead;
c. loading the beads in wells, each well comprising a single bead; and generating a pyrophosphate signal.

In the first step (a), sequencing adaptors are ligated to fragments within the combination library. Said sequencing adaptor includes at least a region for annealing to a complementary oligonucleotide bound to a bead, a sequencing primer region and a PCR primer region. Thus, adapted fragments are obtained.

In the first step, adapted fragments are annealed to the beads, each bead annealing with a single adapted fragment. To the pool of adapted fragments, beads are added in excess as to ensure annealing of one single adapted fragment per bead for the majority of the beads (Poisson distribution). In the present invention, the adapters that are ligated to the restriction fragments obtained from the clones may comprise a section that is capable of annealing to a bead.

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched, i.e. separated from beads not containing amplified fragments.

In a following step, the enriched beads are loaded in wells, each well comprising a single bead. The wells are preferably part of a PicoTiter™ Plate allowing for simultaneous sequencing of a large number of fragments. After addition of enzyme-carrying beads, the sequence of the fragments is determined using pyrosequencing. In successive steps, the PicoTiter™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on www.biotagebio.com; www.pyrosequencing.com/section technology. The technology is further applied in e.g. WO 03/004690, WO 03/054142, WO 2004/069849, WO 2004/070005, WO 2004/070007, and WO 2005/003375 (all in the name of 454 Life Sciences), and Margulieset al., nature 2005, 437, 376-380, which are herein incorporated by reference.

In the present invention, the beads are preferably equipped with primer sequences or parts thereof that are capable of being extended by polymerisation to yield bead-bound amplicons. In other embodiments, the primers used in the amplification are equipped with sequences, for instance at their 5'-end, that allow binding of the amplicons to the beads in order to allow subsequent emulsion polymerisation followed by sequencing. Alternatively, the amplicons may be ligated with sequencing adaptors prior to ligation to the beads or the surface. The sequenced amplicons will reveal the identity of the identifier and hence the combination of identifiers reveals the identity of the clone.

Solexa Technologies

One of the methods for high throughput sequencing is available from Solexa, United Kingdom (www.solexa.co.uk) and described inter alia in WO0006770, WO0027521, WO0058507, WO123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005068089, WO2005078130. In essence, the method starts with adaptor-ligated fragments of DNA, in this particular case of adapter-ligated restriction fragments of the artificial chromosome pools as described herein elsewhere. The adaptor-ligated DNA is randomly attached to a dense lawn of primers that are attached to a solid surface, typically in a flow cell. The other end of the adaptor ligated fragment hybridizes to a complementary primer on the surface. The primers are extended in the presence of nucleotides and polymerases in a so-called solid-phase bridge amplification to provide double stranded fragments. This solid phase bridge amplification may be a selective amplification. Denaturation and repetition of the solid-phase bridge amplification results in dense clusters of amplified fragments distributed over the surface. The sequencing is initiated by adding four differently labelled reversible terminator nucleotides, primers and polymerase to the flow cell. After the first round of primer extension, the labels are detected, the identity of the first incorporated bases is recorded and the blocked 3' terminus and the fluorophore are removed from the incorporated base. Then the identity of the second base is determined in the same way and so sequencing continues.

In the present invention, the adaptor-ligated restriction fragments or the amplicons are bound to the surface via the primer binding sequence or the primer sequence. The sequence is determined as outlined, including the identifier sequence and (part of) the restriction fragment. Currently available Solexa technology allows for the sequencing of fragments of about 25 base pairs. By economical design of the adaptors and the surface bound primers, the sequencing step reads through the sample identifier, the remains of the recognition sequence of the restriction endonuclease and any optional selective bases. When a 6 bp sample identifier is used, the remains are from the rare cutter EcoRI (AACCT), the use of two selective bases yields an internal sequence of the restriction fragment of 12 bp that can be used to uniquely identify the restriction fragment in the sample.

In a preferred embodiment based on the Solexa sequencing technology above, the amplification of the adapter ligated restriction fragments is performed with a primer that contains at most one selective nucleotide at its 3'end, preferably no selective nucleotides at is 3' end, i.e. the primer is only complementary to the adaptor (a +0 primer).

In alternative embodiments directed to the sequencing methods described herein, the primers used in the amplification may contain specific sections (as alternative to the herein described primer or primer binding sequences) that are used in the subsequent sequencing step to bind the adaptor-capped restriction fragments or amplicons to the surface. These are generally depicted as the key region or the 5'-primer compatible sequence.

The present invention further embodies itself in adaptors containing pool-specific or degenerated identifier sections and/or in primers containing pool-specific identifiers, respectively.

EXAMPLES

De Novo BAC-Based Physical Map Construction of *Arabidopsis Thaliana* Based on a Sequencing By Synthesis (SBS) Approach This example is based on the following generalisations.

The total *Arabidopsis thaliana* genome is ~125 Mbp. A Bacterial Artificial Chromosome (BAC) has a genomic insert of ~100 kb on average. One Genome Equivalent (GE) of BACs for a 1× physical coverage of the *Arabidopsis* genome comprises ~1250 BACs. For optimal results, it is preferred that the construction of the BAC pools is such that one BAC pool contains not more than 0.34 GE (~384 BACs). Statistical analysis predicts that in 0.34 GE the chance of finding 2 identical BACs (that is 2 BACs that would map to the exact same physical position) is <5%. Lower GE' in a BAC pool further reduces the chance of finding two BACs mapping to the same position. A straightforward 3D-pooling system is used for the calculations. A total of 10 GE of BACs of 2 different high quality BAC libraries (2 different cloning enzymes eg. EcoRI and HindIII) are sufficient for the construction of a high quality physical map. 10 GE BACs for *Arabidopsis* is ~12.500 BACs.

The sequence Tags (the combination of part of the restriction fragment and identifier) are generated from a rare cutter restriction site, for example AFLP fragments such as EcoRI/MseI, or HindIII/MseI or a combination of several enzyme combinations (ECs).

In this example the enzyme combination HindIII/MseI is used. The distribution of HindIII/MseI fragments in the *Arabidopsis* genome is estimated to be between 50 to 120 fragments per 100 kb.

Figure 1:
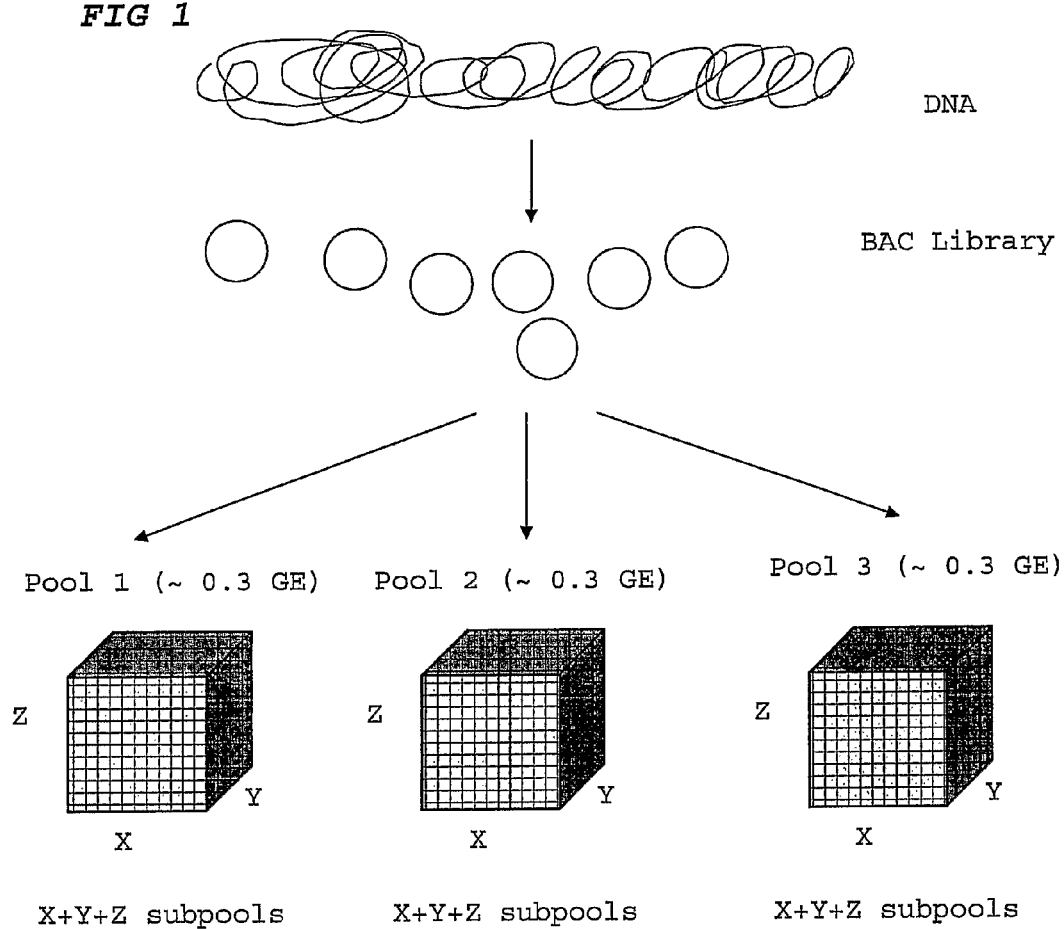
FIG. 1: Schematic representation of pooling strategies.
Figure 2:
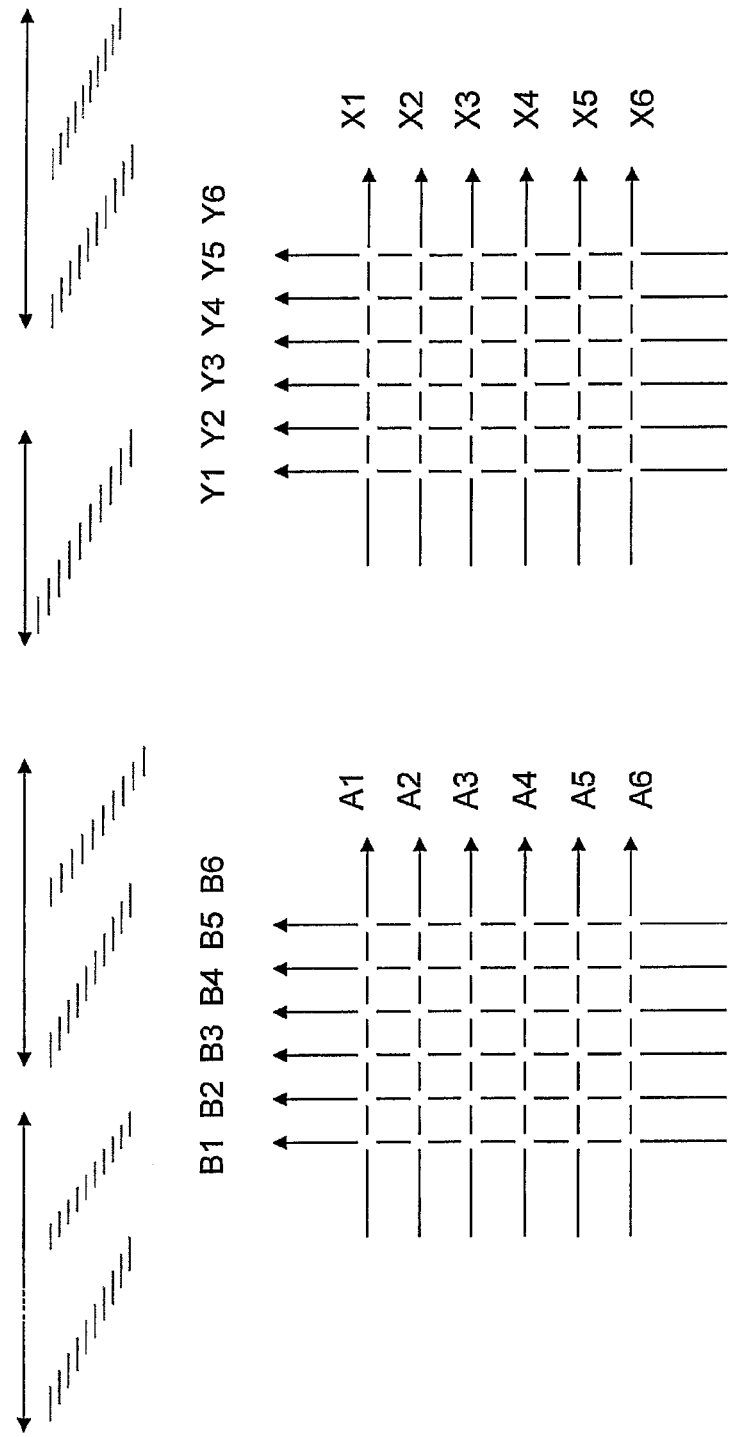
FIG. 2: Four continous BAC-contigs on *Arabidopsis* chromosome 4-pooling strategy
Figure 3:
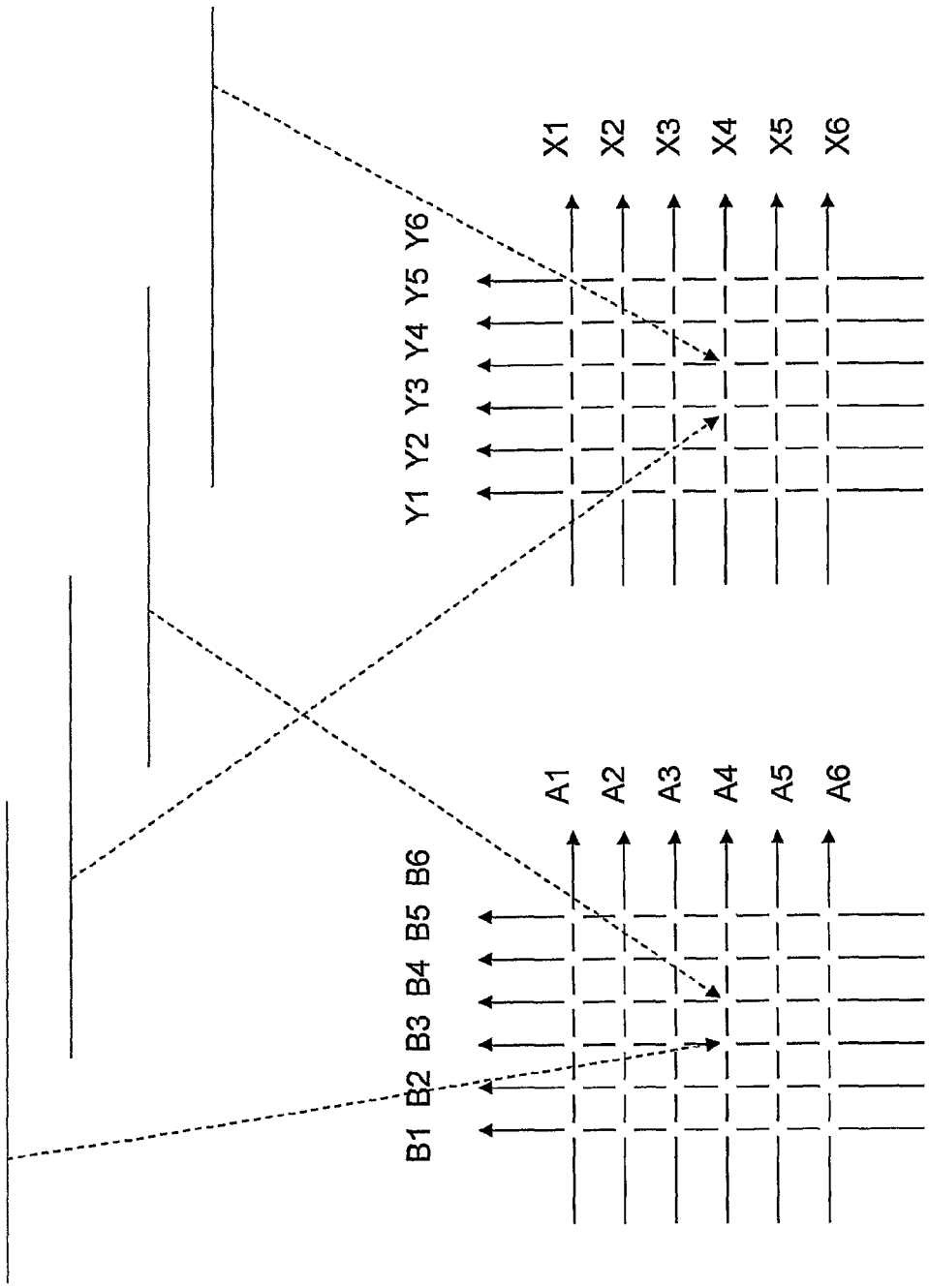
FIG. 3: No overlaps within the group, alternating minimal tiling path

Set up for high throughput sequencing:

See also FIG. 1. 0.3 GE corresponds to 384 BACs. 3D-pooling of 384 BACs, with dimensions X+Y+Z results in 8+12+4=24 subpools. For 10 GE:M (X+Y+Z)=30 (8+12+4)= 720 subpools.

For each subpool, the aim is to generate:
100 sequenced Tags per BAC
10 fold sequence redundancy per Tag
3 dimensional pooling (each BAC fragment is sequenced in each (X,Y,Z) dimension)

This means that for bridging amplification-based high throughput sequencing of a pool of 0.34GE, a set of sequencing reads of: 8 subpools×(12×4×100×10)+12 subpools×(8× 4×100×10)+4 subpools×(12×8×100×10)=1.152.000 reads are needed. This means for one GE that 3*1.152.000=3.456.000 reads per GE are needed and 10×3.456.000 reads per 10 GE=34.560.000 reads.

A single BAC generates a potential of ~100 unique sequence tags of ~20 bps (including the restriction site). The number of sequences will depend on the choice and/or combination of enzyme combinations.

The individual BAC coordinates and accompanying sequence tags can be deduced from the addressed subpool sequences by the "deconvolution" step. Consequently, via deconvolution each sequence tag is assignable to the corresponding individual BAC. Repetitive sequence tags are ignored. The deconvolution process will result in a string of 100 Tags per BACs, and subsequently the assembly of a de novo physical map is achieved through a FPC (FingerPrintedContigs) type process, as described by Cari Soderlund for BAC fragments analysed in agarose gels (Soderlund et al. 2000—Genome Research 10; 1772-1787). Finally, the anchoring of the physical map to the genetic map is performed in silico. For larger genomes other pooling strategies may be necessary.

De Novo BAC-Based Physical Map Construction of *Cucumis Sativus* Based on a Sequencing By Synthesis (SBS) Approach This example is based on the following generalisations.

The total *Cucumis sativus* genome is ~350 Mbp. A Bacterial Artificial Chromosome (BAC) has a genomic insert of ~100 kb on average. One Genome Equivalent (GE) of BACs for a 1× physical coverage of the *Arabidopsis* genome comprises ~3500 BACs. For optimal results, it is preferred that the construction of the BAC pools is such that one BAC pool contains not more than 0.34 GE (~384 BACs). Statistical analysis predicts that in 0.34 GE the chance of finding 2 identical BACs (that is 2 BACs that would map to the exact same physical position) is <5%. Lower GE' in a BAC pool further reduces the chance of finding two BACs mapping to the same position. A straightforward 3D-pooling system is used for the calculations. A total of 10 GE of BACs of 2 different high quality BAC libraries (2 different cloning enzymes eg. EcoRI and HindIII) are sufficient for the construction of a high quality physical map. 10 GE BACs for Cucumis is 35.000 BACs.

The sequence Tags (the combination of part of the restriction fragment and identifier) are generated from a rare cutter restriction site, for example AFLP fragments such as EcoRI/MseI, or HindIII/MseI or a combination of several enzyme combinations (ECs).

In this example the enzyme combination HindIII/MseI is used. The distribution of HindIII/MseI fragments in the *Cucumis sativus* genome is estimated to be between 50 to 120 fragments per 100 kb.

Set up for high throughput sequencing:

See also FIG. 1. 0.3 GE corresponds to 1152 BACs. 3D-pooling of 1152 BACs, with dimensions X+Y+Z results in 8+12+12=32 subpools. For 10 GE:M (X+Y+Z)=30(8+12+12)=960 subpools.

For each subpool, the aim is to generate:
100 sequenced Tags per BAC
10 fold sequence redundancy per Tag
3 dimensional pooling (each BAC fragment is sequenced in each (X,Y,Z) dimension)

This means that for bridging amplification-based high throughput sequencing of a pool of 0.34GE, a set of sequencing reads of: 8 subpools×(12×12×100×10)+12 subpools×(8×12×100×10)+12 subpools×(12×8×100×10)=3.456.000 reads are needed. This means for one GE that 3*3.456.000=10.368.000 reads per GE are needed and 10×10.368.000 reads per 10 GE=103.680.000 reads.

A single BAC generates a potential of ~100 unique sequence tags of ~20 bps (including the restriction site). The number of sequences will depend on the choice and/or combination of enzyme combinations.

The individual BAC coordinates and accompanying sequence tags can be deduced from the addressed subpool sequences by the "deconvolution" step. Consequently, via deconvolution each sequence tag is assignable to the corresponding individual BAC. Repetitive sequence tags are ignored. The deconvolution process will result in a string of 100 Tags per BACs, and subsequently the assembly of a de novo physical map is achieved through a FPC (FingerPrintedContigs) type process, as described by Cari Soderlund for BAC fragments analysed in agarose gels (Soderlund et al. 2000—Genome Research 10; 1772-1787). Finally, the anchoring of the physical map to the genetic map is performed in silico. For larger genomes other pooling strategies may be necessary.

AFLP templates (EcoRI/MseI or HindIII/MseI) are prepared from pooled BACs. AFLP amplification is performed using a combination 2 HindIII+1 primers and an MseI+0 primer (same for EcoRI). The use of two +1 primer ensures amplification of approximately 50% of the H/M (or E/M) fragments from the pools, i.e. on average 70/2=35 restriction fragments are amplified for each enzyme combination. The AFLP amplification reactions are performed with AFLP primers containing unique identifier tags at the 5'end for each of the BAC pools. Hence at least 74 identifier sequences are needed. This can be accomplished with 4 base tags ($4^4$=256 possibilities). Identifier sequences are only needed for the HindIII primer, since unidirectional sequencing will be performed in this example.

AFLP reaction mixtures of all pools are mixed in equal amounts, creating a fragment library. The fragment library is used to construct a sequence library.

Given a 3-D pooling strategy, this means that every fragment is sampled a plurality of times on average in each dimension. Results are 100 bp sequences derived from the HindIII (or EcoRI) site of the restriction fragments. As said, per BAC clone an average of 35 sequences are obtained. The sequences form the basis for contig assembly using a procedure similar to FPC (Software package by Soderlund obtainable from http:www.agcol.arizona.edu/software/fpc/) but based on sequence matching (more detailed).

The advantage of the use of reproducible complexity reduction is that less fragments are needed for the construction of a physical map. A complexity reduction of 50% in the above Cucumis example leads to 51.840.000 reads instead of 103.680.000. A further advantage of the present invention is, using complexity reduction as described herein, that physical maps can be generated of controllable quality. This means that by reducing a BAC pool in complexity by a +1 AFLP amplification, for instance a primer combination with +C, results in a physical map of about 25% of the quality (coverage) compared to a +1 amplification with all four primer combinations (A, C, T, G). However, when two or three primer combinations are used, increased coverage is obtained, i.e. for instance 55% or 90%, respectively, compared to the coverage obtained with a +1 amplification with all four primer combinations (A, C, T, G).

BAC Clones Addresses:

Fragments derived from the same BAC clone are amplified with 3 different tagged primers. Hence, unique sequences observed in combination with 3 tags are assigned to a single BAC clone in the library. Repeated sequences are observed in combinations with multiple tags and can therefore not be connected to a single BAC clone. This affects a considerable proportion of the fragments, but among 35 fragments/BAC clone, at a least a subset is unique.

A 10-fold sequence coverage of the BAC pools (3.3 fold/dimension) means that not all expected fragments are observed (due to concentration differences of individual clones and sampling variation etc). Hence a fraction of the (unique) sequences is only observed in combination with 1 or 2 tags (or not at all), which precludes assigning them to a single BAC clone. However, to the extent that this is due to sampling variation between the restriction fragments derived from the same clone, the fact that 35 fragments are sampled means that the combination of tags provides the correct address for the BAC: see below.

|  | Tag 1 | Tag 2 | Tag 3 |
|---|---|---|---|
| Fragment 1 | X | X |  |
| Fragment 2 |  | X | X |
| Fragment 3 |  | X | X |
| Fragment 4 | X |  | X |
| Fragment 5 | X | X | X |
| Etc. |  |  |  |
| Fragment 35 | X | X |  |

The scheme above illustrates that contig building groups the fragments together in a contig; fragment 5, which has a unique sequence and was sampled in combination with 3 tags defines the address of the BAC in library, from which fragment 1-4 (+35) are probably derived as well.

Hence, the strength of the approach is that sequence information on a sufficiently large number of restriction fragments (35 in the above example) is used to build accurate contigs, while the use of a 3 dimensional tagging system allow direct identification for the majority of BACs, even though the BAC address can not be derived from each individual fragment sequence (due to experimental variation). However, the combination of tags from fragments derived from the same BAC will provide the BAC address.

Thus, the information derived from sequence-based BAC contiging is the same as for conventional approaches (i.e. contig+BAC address). It is observed that for individual clone fingerprinting approaches, the BAC address will be known by definition.

Example 2

Procedure for High Throughput Physical Mapping by Sequence tag BAC Mapping.

A total of 72 BACs (BAC=Bacterial Artificial Chromosome) mapping to chromosome 4 of *Arabidopsis* and spanning a total physical stretch of 5.4 Mb in 4 BAC contigs (1.8 Mb, 1.2 Mb, 0.5 Mb and 1.9 Mb) were selected from the TAIR and other databases. The donor plant of the BAC libraries is *Arabidopsis thaliana* ecotype Colombia. The 72 BACs, ranging in size between 70 kb and 150 kb, were separated in 2 groups of 36 BACs, group "AB" and group "XY". Within the 2 groups the 36 BACs have no internal overlap, while the BACs of group AB and group XY combined can be assembled into 4 continuous minimal tiling path contigs with alternating BACs from group AB and XY (see FIGS. 2-5).

Pooling Strategy for 72 *Arabidopsis* BACs, 36 in Group AB and 36 in Group XY

GroupAB

|    | B1     | B2     | B3     | B4     | B5     | B6     |
|----|--------|--------|--------|--------|--------|--------|
| A1 | F23J03 | T30A10 | T25P22 | T09A04 | T05L19 | F07L13 |
| A2 | T12H20 | T22B04 | F25E04 | T26M18 | T04C09 | F07K02 |
| A3 | F07K19 | F16G20 | T32A16 | T22A06 | F06i07 | F24A06 |
| A4 | F08F16 | F28M20 | F10N07 | F08B04 | T16i18 | F04i10 |
| A5 | T16L01 | F17i05 | F28A23 | T04L20 | T12J05 | F23E12 |
| A6 | F14H08 | T19P05 | T10C14 | F06D23 | T03E09 | T06O13 |

GroupXY

|    | Y1     | Y2     | Y3     | Y4     | Y5     | Y6     |
|----|--------|--------|--------|--------|--------|--------|
| X1 | T03H13 | T08A17 | T15G18 | F17A08 | F28M11 | F24G24 |
| X2 | T04F09 | F25i24 | F08L21 | T05C23 | F16J13 | T01P17 |
| X3 | T12H17 | F21P08 | F09D16 | T19F09 | F22K18 | F13M23 |
| X4 | T30C03 | F03L17 | F11C18 | F10M06 | F04D11 | F26P21 |
| X5 | F17M05 | T09O24 | T04G07 | F10M10 | F11i11 | T04K12 |
| X6 | F05M05 | T19K04 | F23E13 | T02G10 | F07O06 | T08H13 |

T = TAMU BAC library - 12.5 microgram chloramphenicol/ml
F = IGF BAC library - 50 microgram kanamycine/ml The 72 BACs were grown overnight as individual clones in 200 microliter standard TY medium including chloramphenicol (TAMU BAC clones) or kanamycine (IGF BAC clones). All clones were grown in a 6×6 format to facilitate the pooling procedure. In the morning the liquid culture was pooled in 2 dimensions (6×6) such that 12 pools per group were generated. Each pool contained 600 microliter of medium with grown BACs (100 microliter per individual BAC). DNA was isolated from all 24 BAC pools following a standard alkaline miniprep procedure according to Sambrook et al. (2001).

50 ng DNA of each BAC pool was digested with restriction enzymes EcoRI and MseI, and subsequently EcoRI and MseI AFLP adaptors were ligated, according to the standard AFLP procedure described by Vos et al. (1995). The restriction/ligation mix was diluted 10× in MilliQ-water and 5 microliter was used in the amplification step. The primers used in the amplification step were designed with a 4 nucleotide recognition sequence, such that each pool is tagged with a pool specific 4 nucleotide address-sequence. This recognition sequence is necessary to facilitate the deconvolution of all sequences to an individual BAC-coordinate.

Figure 4:
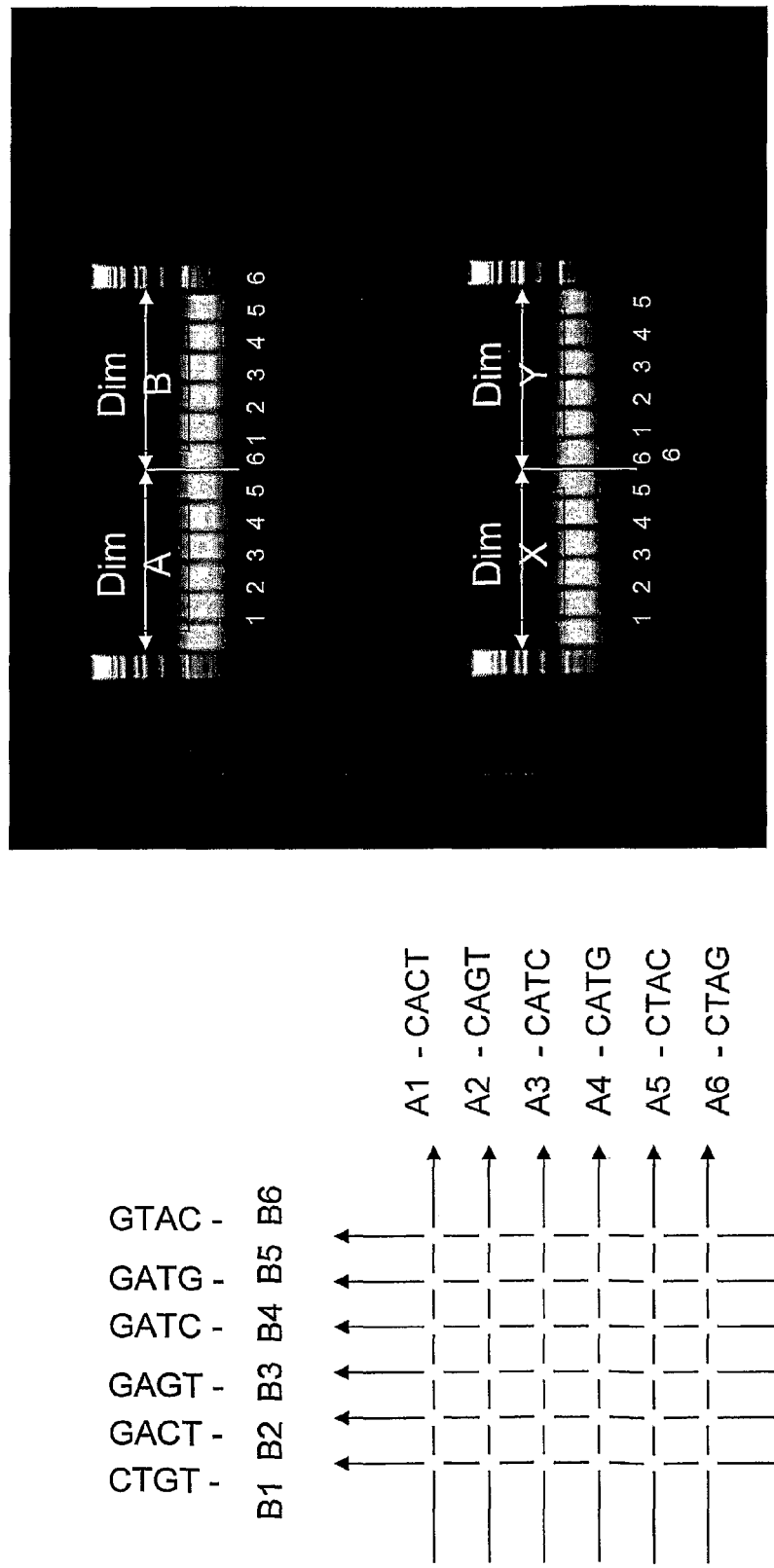
FIG. 4: recognition sequence adressed BAC pools—amplified product on agarose-gel
Figure 5:
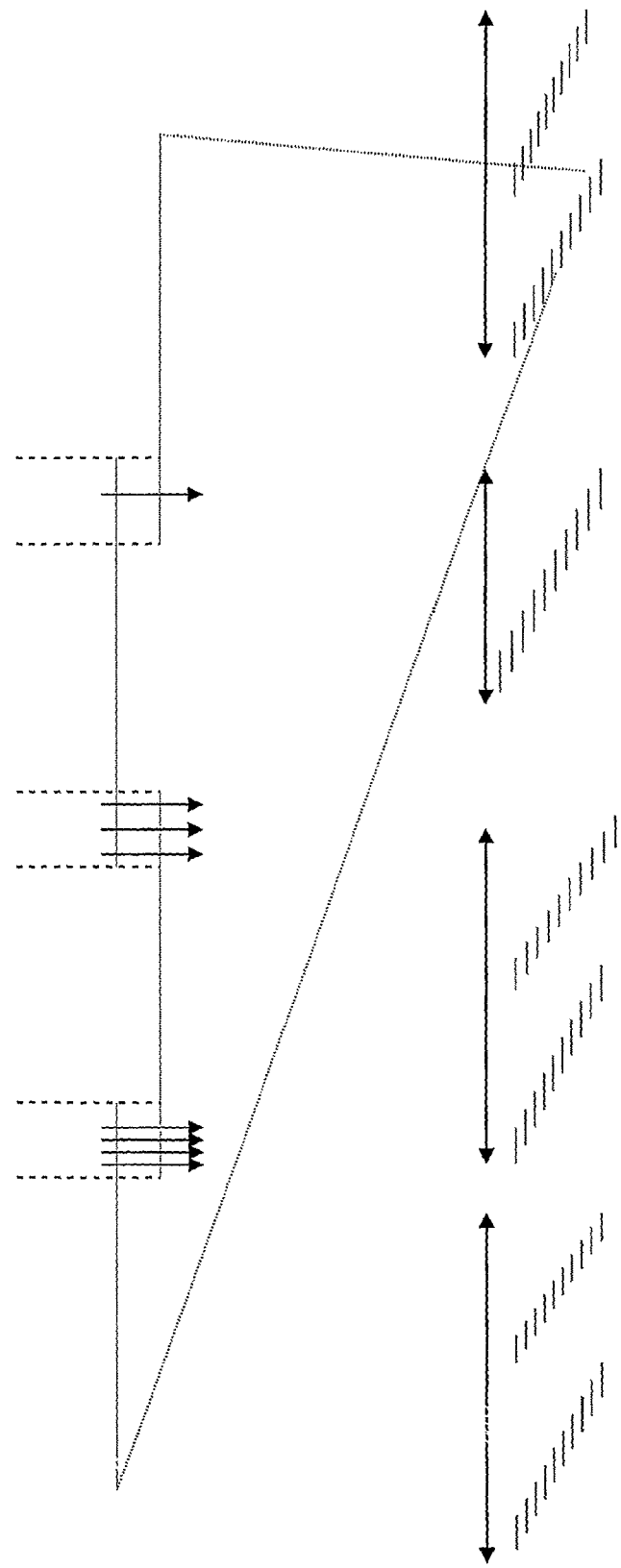
FIG. 5: Re-assembled minimal tiling path-part of the 1.9 Mb contig enlarged

Both the EcoRI+0 and MseI+0 primers used were adapter compatible 5'-phosphorylated primers carrying 5'-recognition sequences and are different for each pool coordinate (see FIG. 4). The 5'-phosphorylation is necessary for the ligation of the pyrosequencing adaptors. Amplification was performed for 30 cycli with the profile: 94° C. (30 sec), 56° C. (60 sec), 72° C. (60 sec). After amplification the products were checked on agarose gel (FIG. 4) and the 12 amplified pool-products of each group were pooled into a group-pool (AB cq. XY) and quantified. Five micrograms DNA of each group-pool was immediately processed in the further preparation steps for 454 sequencing. 454 pyrosequencing was performed on the GS20 platform according to Margulies et al. (2005).

Analysis of the Dataset and Assembly of the BAC Contigs

The list of DNA sequence reads as generated by the GS20 pyrosequencing machine were parsed in 3 steps:

Step 1) the first 4 nucleotides consisting of the pool sample code were identified and the corresponding pool-labels were assigned. If the code was unknown, the read was removed from the set.

Step 2) the next 16 or 17 nucleotides (depending on the restriction enzyme) containing the primer sequence were identified. When 100% identical to the primer sequence the reads were approved and added to the dataset and otherwise removed.

Step 3) all reads from step 2 were trimmed to 14 nucleotides after the primer sequence.

All correct trimmed sequence reads were subsequently grouped: all 100% identical reads were identified and assigned to their corresponding pool. Each unique group of reads is termed a 'tag'. Tags that were found in exactly 2 pools, both one for the X-coordinate and one for the Y-coordinate, were linked to a specific BAC: this procedure is called deconvolution.

All unique tags for deconvolved BACs were listed for both BAC groups. Pairs of BACs with one or more common tags were identified. Subsequently the BAC contigs could be assembled as shown in table 1.

TABLE 1

BAC links from all sequence tags, common between pairs of BACs (e.g. X1Y1 and A1B1) and occurring at least 2 times in each pool. Contigs are numbered.

| BAC link   | NrTags | Contig  |
|------------|--------|---------|
| X1Y1__A1B1 | 8      | Contig1 |
| X1Y2__A1B1 | 18     | Contig1 |
| X1Y2__A1B2 | 6      | Contig1 |
| X1Y3__A1B2 | 19     | Contig1 |
| X1Y3__A1B3 | 3      | Contig1 |
| X1Y4__A1B3 | 10     | Contig1 |
| X1Y4__A1B5 | 10     | Contig1 |
| X1Y5__A1B4 | 16     | Contig1 |
| X1Y5__A1B5 | 12     | Contig1 |
| X1Y6__A1B4 | 13     | Contig1 |
| X1Y6__A1B6 | 4      | Contig1 |
| X2Y1__A1B6 | 1      | Contig1 |
| X2Y1__A2B1 | 3      | Contig1 |
| X2Y2__A2B1 | 4      | Contig1 |
| X2Y2__A2B2 | 2      | Contig1 |
| X2Y3__A2B2 | 5      | Contig1 |
| X2Y4__A2B3 | 4      | Contig2 |
| X2Y4__A2B4 | 2      | Contig2 |
| X2Y5__A2B4 | 1      | Contig2 |
| X2Y5__A2B5 | 1      | Contig2 |
| X2Y6__A2B5 | 4      | Contig2 |
| X3Y1__A2B6 | 3      | Contig3 |
| X3Y1__A3B1 | 5      | Contig3 |
| X3Y2__A3B1 | 4      | Contig3 |
| X3Y2__A3B2 | 2      | Contig3 |
| X3Y3__A3B2 | 1      | Contig3 |
| X3Y3__A3B3 | 5      | Contig3 |
| X3Y4__A3B3 | 15     | Contig3 |
| X3Y4__A3B4 | 1      | Contig3 |

TABLE 1-continued

BAC links from all sequence tags, common between pairs of BACs (e.g. X1Y1 and A1B1) and occurring at least 2 times in each pool. Contigs are numbered.

| BAC link | NrTags | Contig |
|---|---|---|
| X3Y5_A3B4 | 2 | Contig3 |
| X3Y5_A3B5 | 13 | Contig3 |
| X3Y6_A3B5 | 7 | Contig3 |
| X3Y6_A3B6 | 7 | Contig3 |
| X4Y1_A3B6 | 10 | Contig3 |
| X4Y2_A4B1 | 12 | Contig4 |
| X4Y2_A4B2 | 4 | Contig4 |
| X4Y3_A4B2 | 5 | Contig4 |
| X4Y3_A4B3 | 20 | Contig4 |
| X4Y4_A4B3 | 5 | Contig4 |
| X4Y4_A4B4 | 11 | Contig4 |
| X4Y5_A4B5 | 9 | Contig5 |
| X4Y6_A4B5 | 7 | Contig5 |
| X4Y6_A4B6 | 6 | Contig5 |
| X5Y1_A5B1 | 6 | Contig6 |
| X5Y2_A5B1 | 5 | Contig6 |
| X5Y2_A5B2 | 28 | Contig6 |
| X5Y3_A5B2 | 4 | Contig6 |
| X5Y3_A5B3 | 26 | Contig6 |
| X5Y4_A5B4 | 4 | Contig7 |
| X5Y5_A5B4 | 3 | Contig7 |
| X5Y5_A5B5 | 1 | Contig7 |
| X5Y6_A5B5 | 16 | Contig7 |
| X5Y6_A5B6 | 19 | Contig7 |
| X6Y1_A5B6 | 7 | Contig7 |
| X6Y1_A6B1 | 14 | Contig7 |
| X6Y2_A6B1 | 3 | Contig7 |
| X6Y2_A6B2 | 14 | Contig7 |
| X6Y3_A6B2 | 14 | Contig7 |
| X6Y3_A6B3 | 8 | Contig7 |
| X6Y4_A6B3 | 14 | Contig7 |
| X6Y5_A6B5 | 13 | Contig8 |
| X6Y6_A6B5 | 8 | Contig8 |
| X6Y6_A6B6 | 14 | Contig8 |

It was demonstrated that the 4 BAC minimal tiling paths of 1.8 Mb, 1.2 Mb, 0.5 Mb and 1.9 Mb could be reassembled in a straightforward way after the deconvolution of sequence tags to the individual BACs (table 1 and FIG. 4). A comparison of the generated GS20 tags with predicted fragments in silico showed that 70 to 80% of the EcoRI/MseI fragments were sequenced. Therefore in the reassembly of the 4 BAC contigs some of the smaller physical overlaps between 2 BACs could not be detected.

The fact that short reads (14 bp) are sufficient to reassemble the BAC tiling paths indicates that high throughput sequencing platforms with short read length (such as the Illumina Genome Analyser and SOliD (ABI)) enables high throughput physical map assembly following the proposed method.

The invention claimed is:

1. Method for the generation of a physical map of at least part of a genome comprising the steps of:
   (a) providing a sample DNA;
   (b) generating an artificial chromosome clone bank wherein each artificial chromosome clone contains part of the sample DNA;
   (c) combining the artificial chromosome clones in a plurality of pools, wherein each clone is present in more than one pool of the plurality of pools, to create a library;
   (d) digesting the DNA contained in the plurality of pools with one or more restriction endonucleases to provide for a set of restriction fragments for each pool;
   (e) ligating adaptors to one or both sides of the restriction fragments, wherein at least one adaptor contains a pool-specific identifier or a degenerate identifier section, respectively, to provide adaptor-ligated restriction fragments;
   (f) combining the adaptor-ligated restriction fragments of step (e);
   (g) amplifying the adaptor-ligated fragments with at least one primer to provide amplicons;
   (h) determining the sequence of at least the pool-specific identifier and part of the restriction fragment of the amplicons;
   (i) assigning the restriction fragment sequences determined in the amplicons to the corresponding clones using the pool-specific identifiers;
   (j) building a contig based on sequence matching of the restriction fragment derived sections; and
   (k) ordering the restriction fragments of step (i) to thereby build a clone-contig and generating a physical map.

2. Method according to claim 1, wherein the primer contains a pool-specific section corresponding to the pool-specific identifier section in the adaptor or contains a pool-specific identifier at the position of the degenerate identifier section, respectively, to provide amplified adaptor-ligated restriction fragments or amplicons.

3. Method according to claim 2, wherein the amplified adaptor-ligated restriction fragments or amplicons are combined in a set of combined amplicons.

4. Method according to claim 1, wherein the restriction fragments are assigned to the corresponding clone by clustering adapter-ligated restriction fragments or amplicons that contain identical sequences in the restriction fragments but carry different pool-specific identifiers.

5. Method according to claim 1, wherein the sequencing is carried out by means of high-throughput sequencing.

6. Method according to claim 5, wherein the high-throughput sequencing is performed on a solid support.

7. Method according to claim 5, wherein the high-throughput sequencing is based on Sequencing-by-Synthesis.

8. Method according to claim 5, wherein the high-throughput sequencing comprises the steps of:
   annealing the adapter-ligated restriction fragments or amplicons to beads, each bead annealing with a single adapter-ligated restriction fragment or amplicon;
   the beads in water-in-oil micro reactors, each water-in-oil icro reactor comprising a single bead;
   performing emulsion PCR to amplify adapter-ligated restriction fragments or amplicons on the surface of heads;
   optionally, selecting/enriching beads containing amplified amplicons;
   loading the heads in wells, each well comprising a single head; and
   generating a pyrophosphate signal.

9. Method according to claim 5, wherein the high-throughput sequencing comprises the steps of:
   annealing the adapter-ligated restriction fragments or amplicons to a surface containing first and second primers or first and second primer binding sequences respectively,
   performing bridge amplification to provide clusters of amplified adapter-ligated restriction fragments or amplified amplicons,
   determining the nucleotide sequence of the amplified adapter-ligated restriction fragments or amplified amplicons using labelled reversible terminator nucleotides.

10. Method according to claim 1, wherein the identifier is from 4-16 bp.

11. Method according to claim 10, wherein the identifier is from 4-10 bp.

12. Method according to claim 11, wherein the identifier is from 4-8 bp.

13. Method according to claim 12, wherein the identifier is from 4-6 bp.

14. Method according to claim 10, wherein the identifier does not contain 2 or more identical consecutive bases.

15. Method according to claim 10, wherein for two or more clones, the corresponding identifiers contain at least two different nucleotides.

16. Method according to claim 1, wherein at least one primer carries 1-10 selective nucleotides at its 3' and to provide for a subset of amplicons.

17. Method according to claim 16, wherein the at least one primer carriers 1-4 selective nucleotides at it 3' end.

* * * * *

UNITED STATES PATENT AND TRADEMARK OFFICE
CERTIFICATE OF CORRECTION

PATENT NO.         : 8,685,650 B2
APPLICATION NO.    : 13/783601
DATED              : April 1, 2014
INVENTOR(S)        : Michael Josephus Theresia Van Eijk and Taco Peter Jesse It is certified that error appears in the above-identified patent and that said Letters Patent is hereby corrected as shown below:

IN THE CLAIMS

Column 18, Claim 8, Line 40, insert --emulsifying-- before "the beads...".

Column 18, Claim 8, Line 44, replace "heads;" with --beads;--.

Column 18, Claim 8, Line 47, replace "heads" with --beads--.

Column 18, Claim 8, Line 48, replace "head" with --bead--.

Column 19, Claim 16, Line 9, replace "3' and" with --3' end--.

Column 19, Claim 17, Line 12, replace "carriers" with --carries--.

Signed and Sealed this
Ninth Day of September, 2014

Michelle K. Lee
*Deputy Director of the United States Patent and Trademark Office*